United States Patent
Chaturvedi

(10) Patent No.: US 11,583,629 B2
(45) Date of Patent: Feb. 21, 2023

(54) ALARM FOR BLOOD BACKFLOW DURING INTRAVENOUS INFUSION

(71) Applicant: International Business Machines Corporation, Armonk, NY (US)

(72) Inventor: Vishal Mani Chaturvedi, Greater Noida (IN)

(73) Assignee: International Business Machines Corporation, Armonk, NY (US)

( * ) Notice: Subject to any disclaimer, the term of this patent is extended or adjusted under 35 U.S.C. 154(b) by 316 days.

(21) Appl. No.: 16/994,720

(22) Filed: Aug. 17, 2020

(65) Prior Publication Data

US 2022/0047809 A1    Feb. 17, 2022

(51) Int. Cl.
*A61M 5/168*  (2006.01)
*G16H 20/17*  (2018.01)
*G16H 40/67*  (2018.01)
*G16H 40/63*  (2018.01)

(52) U.S. Cl.
CPC ........ *A61M 5/16831* (2013.01); *G16H 20/17* (2018.01); *G16H 40/63* (2018.01); *G16H 40/67* (2018.01); *A61M 2205/18* (2013.01); *A61M 2205/50* (2013.01); *A61M 2205/581* (2013.01); *A61M 2205/582* (2013.01); *A61M 2205/584* (2013.01)

(58) Field of Classification Search
None
See application file for complete search history.

(56) References Cited

U.S. PATENT DOCUMENTS

| | | | |
|---|---|---|---|
| 4,176,349 A | 11/1979 | Fliegel | |
| 2003/0140351 A1 | 7/2003 | Hoarty et al. | |
| 2006/0023093 A1* | 2/2006 | Tan | H04N 9/09 |
| | | | 348/E9.006 |
| 2006/0189926 A1* | 8/2006 | Hall | A61B 5/14546 |
| | | | 600/316 |
| 2010/0305499 A1* | 12/2010 | Matsiev | A61M 5/172 |
| | | | 324/693 |

FOREIGN PATENT DOCUMENTS

| | | | | |
|---|---|---|---|---|
| CN | 204446789 U | | 7/2015 | |
| CN | 107441594 A | | 12/2017 | |
| CN | 206730224 U | * | 12/2017 | ............ A61M 15/44 |
| CN | 110136195 A | | 8/2019 | |
| CN | 210494738 U | | 5/2020 | |

(Continued)

OTHER PUBLICATIONS

CN 2067302224 translation (Year: 2017).*

(Continued)

*Primary Examiner* — Manuel A Mendez
(74) *Attorney, Agent, or Firm* — David B. Woycechowsky

(57) ABSTRACT

A red, green, and blue values for a fluid are received. A standard red, green, and blue values for the fluid are determined. A tolerance red, green, and blue values are determined for the fluid based on the standard red, green, and blue value for the fluid. An updated red, green, and blue values for the fluid are received. Whether any of the updated red, green, and blue values for the fluid are outside of the associated tolerance red, green, and blue values for the fluid is determined.

14 Claims, 3 Drawing Sheets

(56) References Cited

FOREIGN PATENT DOCUMENTS

| EP | 0498624 B1 | 8/1992 |
|---|---|---|
| IN | 201841017233 A | 5/2018 |

OTHER PUBLICATIONS

Ajayan et al., "Smart Drip Using Arduino Microcontroller", JCSE International Journal of computer Sciences and Engineering, vol. 7,Issue-6, Jun. 2019, E-ISSN:2347-2693, 8 pages.

Du et al., "Novel Wearable Device for Blood Leakage Detection during Hemodialysis Using an Array Sensing Patch." Sensors (Basel, Switzerland) vol. 16,6 849. Jun. 9, 2016, 15 pages, doi:10.3390/s16060849,<https://www.ncbi.nlm.nih.gov/pmc/articles/PMC4934275>.

Keerthana, K et al., "A Survey of Systems Used in the Monitoring and Control of Intravenous Infusion", International Journal of Engineering and Technology (IJET), vol. 11 No. 1, ISSN 2319-8613, Feb.-Mar. 2019, 6 pages.

Ray et al., "Novel implementation of IoT based non-invasive sensor system for real-time monitoring of intravenous fluid level for assistive e-healthcare", Circuit World, ISSN:0305-6120, Publication Date, Aug. 5, 2019, 2 Pages, <https://www.emerald.com/insight/content/doi/10.1108/CW-01-2019-0008/full/html>.

Sonotec Ultrasonic Solutions, "BLD | Blood Leak Detector", Last printed Mar. 13, 2020, 4 Pages, <https://www.sonotec.eu/products/non-invasive-fluid-monitoring/blood-leak-detection/blood-leak-detector-bld/>.

"Patent Cooperation Treaty PCT Notification of Transmittal of the International Search Report and the Written Opinion of the International Searching Authority, or the Declaration", Applicant's file reference PF210455PCT, International Application No. PCT/CN2021/112739, International Filing Date 16. Aug. 2021, dated Nov. 11, 2021, 10 Pgs.

"TCS3472 Color Light-to-Digital Converter with IR Filter", Texas Advanced Optoelectronic Solutions Inc., Aug. 2012, 26 pgs.

"What is IV Therapy? Uses, Benefits, Ingredients and Adverse Effects Explained", Drip Hydration, Downloaded from the Internet on Oct. 24, 2022, 30 pgs.,<https://driphydration.com/how-do-iv-drips-work-science-methodology>.

Shelishiyah, et al., "A System to Prevent Blood Backflow in Intravenous Infusions", Abstract Only, 2015 International Conference on Innovations in Information, Embedded and Communication Systems (ICIIECS), 2015, 4 pgs., doi: 10.1109/ICIIECS.2015.7193020.

Wikipedia Contributors, "Intravenous Therapy", From Wikipedia, the free encyclopedia, Downloaded from the Internet on Oct. 24, 2022, Last updated on Oct. 13, 2022, 19 pgs., <https://en.wikipedia.org/wiki/Intravenous_therapy>.

\* cited by examiner

ALARM FOR BLOOD BACKFLOW DURING INTRAVENOUS INFUSION

BACKGROUND

The present invention relates generally to the field of intravenous infusion, and more particularly to a color sensor-based system to alarm block backflow during intravenous (IV) infusion.

Intravenous (IV) therapy delivers fluids directly into a vein. IV therapy can be administered using two approaches: injections and infusions. IV injections typically use a syringe that has a higher pressure than the vein, therefore the pressure difference causes the fluids to flow into the vein. IV infusions use the pressure supplied by gravity to cause the fluids to flow into the vein. IV therapy is the fastest way to deliver medication and fluid replacement throughout the body. Additionally, IV therapy can be sued for fluid volume replacement, to correct electrolyte imbalances, to deliver medications, and/or for blood transfusions.

SUMMARY

Embodiments of the present invention include a computer-implemented method, computer program product, and system for monitoring blood backflow in intravenous therapy. In an embodiment, a red, green, and blue values for a fluid are received. A standard red, green, and blue values for the fluid are determined. A tolerance red, green, and blue values are determined for the fluid based on the standard red, green, and blue value for the fluid. An updated red, green, and blue values for the fluid are received. Whether any of the updated red, green, and blue values for the fluid are outside of the associated tolerance red, green, and blue values for the fluid is determined.

DETAILED DESCRIPTION

Intravenous (IV) therapy delivers fluids directly into a vein. IV therapy bags are designed to let gravity, as opposed to a syringe or other forced technique, carry fluid into the veins over time. IV works because of negative pressure created between the IV chamber and the vein. If the pressure is reversed, blood can flow back into the IV tubing towards the IV chamber. This may happen, for example, when a human bends their arm or a human has higher blood pressure.

Embodiments of the present invention work based on the fact that when there is blood backflow into the IV tubing, there is a change in color of the fluid inside the tube. This change in color can be either due to blood mixed with infusing fluid or blood coming from the body replacing the infusing fluid as fluid is pushed back toward therapy bag. In any of the mentioned possibility a change in color can be detected by a color sensor placed on top of transparent IV tubing. Embodiments of the present invention recognize that the change in color of the fluid can be monitored and an alarm can occur when this color change is greater than a threshold. Embodiments of the present invention recognize that the color of the infusing fluid can be scanned while flowing into the transparent IV tubing and standard red, green, and blue (RGB) values can be determined. Embodiments of the present invention recognize that tolerance levels for the RGB values can be set in order to avoid false alarms in cases of very minor RGB value change due to changes including, but not limited to, light refraction from the tubing, etc.

Embodiments of the present invention provide at least for receiving RGB values. Embodiments of the present invention provide at least for setting standard and tolerance values. Embodiments of the present invention provide at least for receiving updated RGB values. Embodiments of the present invention provide at least for determining whether the updated RGB value is within the tolerance values. Embodiments of the present invention provide at least for waiting a time threshold. Embodiments of the present invention provide at least for indicating an alarm.

Figure 1:
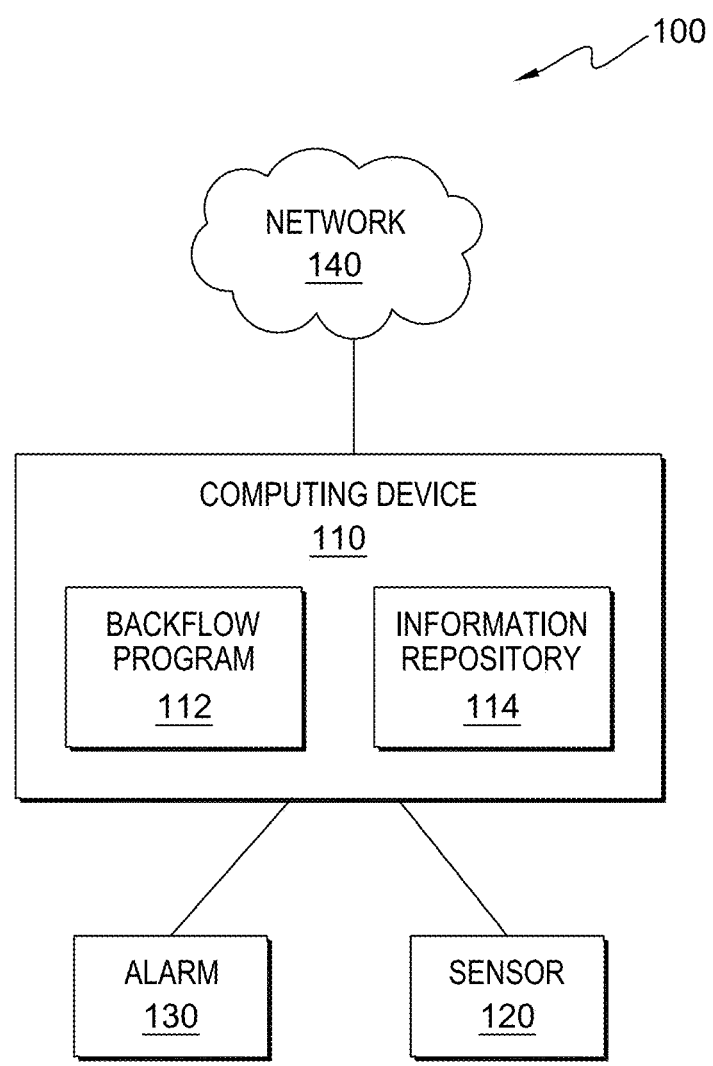
FIG. 1 is a functional block diagram of a network computing environment, generally designated 100, suitable for operation of backflow program 112, in accordance with at least one embodiment of the invention.

Referring now to various embodiments of the invention in more detail, FIG. 1 is a functional block diagram of a network computing environment, generally designated 100, suitable for operation of backflow program 112 in accordance with at least one embodiment of the invention. FIG. 1 provides only an illustration of one implementation and does not imply any limitation with regard to the environments in which different embodiments may be implemented. Many modifications to the depicted environment may be made by those skilled in the art without departing from the scope of the invention as recited by the claims.

Network computing environment 100 includes computing device 110, sensor 120, and alarm 130 interconnected over network 140. In embodiments of the present invention, network 140 can be a telecommunications network, a local area network (LAN), a wide area network (WAN), such as the Internet, or a combination of the three, and can include wired, wireless, or fiber optic connections. Network 140 may include one or more wired and/or wireless networks that are capable of receiving and transmitting data, voice, and/or video signals, including multimedia signals that include voice, data, and video formation. In general, network 140 may be any combination of connections and protocols that will support communications between computing device 110 and other computing devices (not shown) within network computing environment 100.

Computing device 110 is a computing device that can be a laptop computer, tablet computer, netbook computer, personal computer (PC), a desktop computer, a personal digital assistant (PDA), a smartphone, smartwatch, development board microcontroller unit, or any programmable electronic device capable of receiving, sending, and processing data. In general, computing device 110 represents any programmable electronic devices or combination of programmable electronic devices capable of executing machine readable program instructions and communicating with other computing devices (not shown) within computing environment 100 via a network, such as network 140.

In various embodiments of the invention, computing device 110 may be a computing device that can be a standalone device, a management server, a web server, a media server, a mobile computing device, or any other programmable electronic device or computing system capable of receiving, sending, and processing data. In other embodiments, computing device 110 represents a server computing system utilizing multiple computers as a server system, such as in a cloud computing environment. In an embodiment, computing device 110 represents a computing system utilizing clustered computers and components (e.g. database server computers, application server computers, web servers, and media servers) that act as a single pool of seamless resources when accessed within network computing environment 100.

In various embodiments of the invention, computing device 110 includes backflow program 112 and information repository 114. In an embodiment of the present invention, sensor 120 and alarm 130 are shown as separate devices connected to computing device 110. In various embodiments of the invention, computing device 110 may also include (not shown) sensor 120 and alarm 130.

In an embodiment, computing device 110 includes a user interface (not shown). A user interface is a program that provides an interface between a user and an application. A user interface refers to the information (such as graphic, text, and sound) a program presents to a user and the control sequences the user employs to control the program. There are many types of user interfaces. In one embodiment, a user interface may be a graphical user interface (GUI). A GUI is a type of user interface that allows users to interact with electronic devices, such as a keyboard and mouse, through graphical icons and visual indicators, such as secondary notations, as opposed to text-based interfaces, typed command labels, or text navigation. In computers, GUIs were introduced in reaction to the perceived steep learning curve of command-line interfaces, which required commands to be typed on the keyboard. The actions in GUIs are often performed through direct manipulation of the graphics elements.

In an embodiment, computing device 110 includes backflow program 112. Embodiments of the present invention provide for a backflow program 112 that receives RGB values in time period increments and sounds an alarm if the RGB values are not under a threshold. In embodiments of the present invention, backflow program 112 receives initial RGB values. In embodiments of the present invention, backflow program 112 receives standard and tolerance values. In embodiments of the present invention, backflow program 112 receives updated RGB values. In embodiments of the present invention, backflow program 112 determines if the RGB value is under a threshold. In embodiments of the present invention, backflow program 112 waits a time threshold before receiving updated RGB values. In embodiments of the present invention, backflow program 112 provides an alarm.

In an embodiment, computing device 110 includes information repository 114. In an embodiment, information repository 114 may be managed by backflow program 112. In an alternative embodiment, information repository 114 may be managed by the operating system of computing device 110, another program (not shown), alone, or together with, backflow program 112. Information repository 114 is a data repository that can store, gather, and/or analyze information. In some embodiments, information repository 114 is located externally to computing device 110 and accessed through a communication network, such as network 140. In some embodiments, information repository 114 is stored on computing device 110. In some embodiments, information repository 114 may reside on another computing device (not shown), provided information repository 114 is accessible by computing device 110. Information repository 114 may include, but is not limited to, RGB values, standard values, tolerance values, threshold values, and time threshold values.

Information repository 114 may be implemented using any volatile or non-volatile storage media for storing information, as known in the art. For example, information repository 114 may be implemented with a tape library, optical library, one or more independent hard disk drives, multiple hard disk drives in a redundant array of independent disks (RAID), solid-state drives (SSD), or random-access memory (RAM). Similarly, information repository 114 may be implemented with any suitable storage architecture known in the art, such as a relational database, an object-oriented database, or one or more tables.

In an embodiment, computing device 110 is connected directly to sensor 120 via a wired and/or wireless connection. In an alternative embodiment, sensor 120 is connected to computing device 110 via network 140 (not shown). In an embodiment, sensor 120 provides a digital return of red, green, blue, and clear light sensing values. In an embodiment, sensor 120 includes an infrared (IR) blocking filter, integrated on-chip and localized to the color sensing photodiodes that minimizes the IR spectral component of the incoming light and allows color measurements to be made accurately. In an embodiment, sensor 120 is attached to the method of intravenous infusion. For example, sensor 120 is attached to a piece of tubing used for transferring a liquid via intravenous infusion. In an embodiment, the color sensor 120 is placed on top of transparent IV tubing In an embodiment, computing device 110 is connected directly to alarm 130 via a wired and/or wireless connection. In an alternative embodiment, sensor 120 is connected to computing device 110 via network 140 (not shown). In an embodiment, alarm 130 can provide a haptic, audible, and/or visual indication. In an embodiment, alarm 130 may be a device that provides haptic feedback, such as a vibration effect. In an embedment, alarm 130 may be an audible device, such as a speaker. In an embodiment, alarm 130 may be a visual device, such as a light-emitting diode that can be turned on and off. In an alternative embodiment, alarm 130 may provide a visual indication on the display of computing device 110 or any other computer device (not shown) connected to network 140.

As referred to herein, all data retrieved, collected, and used, is used in an opt-in manner, i.e., the data provider has given permission for the data to be used. For example, the received data received and used by backflow program 112 for monitoring blood backflow in IV therapy.

Figure 2:
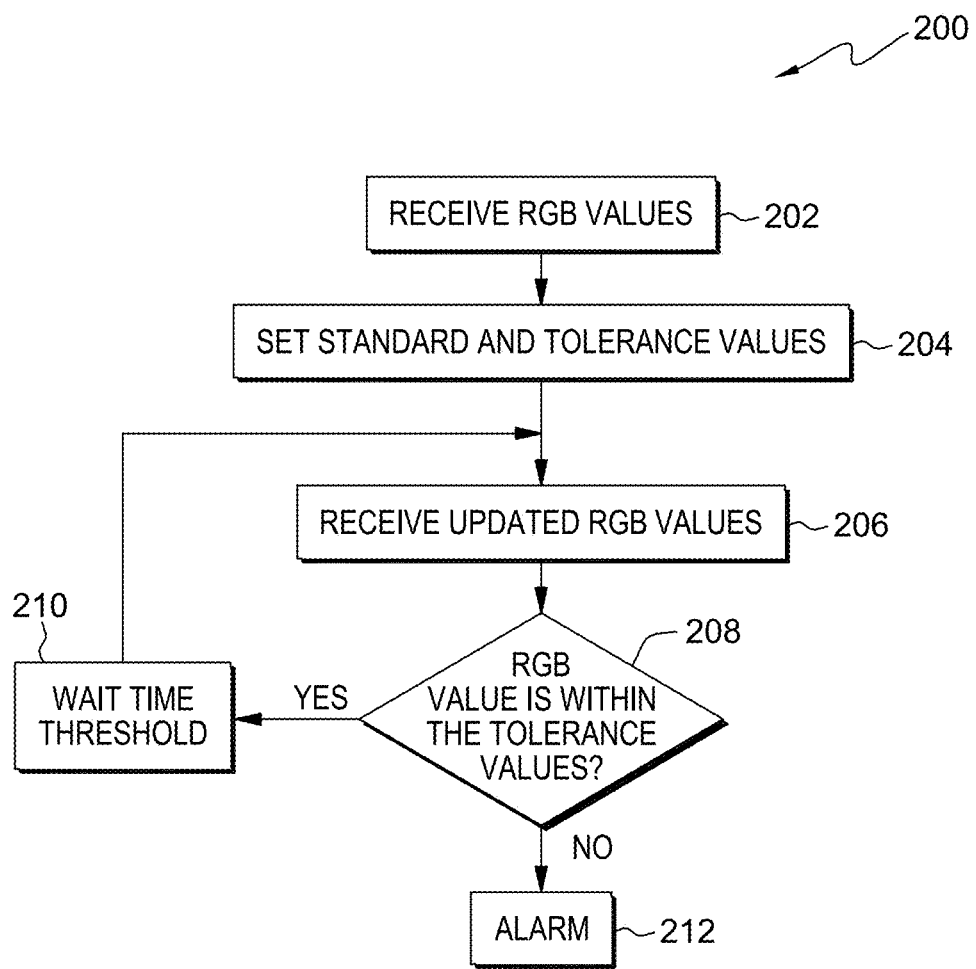
FIG. 2 is a flow chart diagram depicting operational steps for backflow program 112 for monitoring blood backflow in IV therapy, in accordance with at least one embodiment of the invention.

FIG. 2 is a flow chart diagram of workflow 200 depicting operational steps for backflow program 112 in accordance with at least one embodiment of the invention. In an alternative embodiment, the steps of workflow 200 may be performed by any other program while working with backflow program 112. It should be appreciated that embodiments of the present invention provide at least for monitoring blood backflow in IV therapy. However, FIG. 2 provides only an illustration of one implementation and does not imply any limitations with regard to the environments in which different embodiments may be implemented. Many modifications to the depicted environment may be made by those skilled in the art without departing from the scope of the invention as recited by the claims. In a preferred embodiment, a user, via a user interface (not shown), can invoke workflow 200 upon a user wanting backflow program 112 to monitor blood backflow in IV therapy.

Backflow program 112 receives RGB values (step 202). At step 202, backflow program 112 receives RGB values from sensor 120. In an embodiment, the RGB values are initial RGB values. In an embedment, the sensor 120 is attached to a physical IV line that is connected to a human being and providing a fluid to the human being. In an embodiment, sensor 120 determines the RGB values of the fluid in the physical IV line and transmits the RGB values to backflow program 112. In an alternative embodiment, the physical IV line could be connected to an animal and providing a fluid to the animal. In an embodiment, backflow program 112 saves the received RGB values to information repository 114. In an embodiment, RGB values are Red values, Green values, and Blue values. In an embodiment, RGB values range from 0 to 255. In other words, backflow program 112 receives a Red value in the range of 0 to 255, a Green value in the range of 0 to 255, and a Blue value in the range of 0 to 255.

Backflow program 112 sets standard and tolerance values (step 204). At step 204, backflow program 112 determines standard color values and/or tolerance values for the RGB values. In a first embodiment, backflow program 112 sets a standard value for the RGB values based on a user input. In this embodiment, backflow program 112 may receive manual input from a user that indicates a standard RGB value. In other words, backflow program 112 may receive a Red value, a Green value, and a Blue value from user input to set as the standard value. In a second embodiment, backflow program 112 may receive an indication of the fluid being used in the IV therapy. In the second embodiment, backflow program 112 sets a standard value for the RGB values based on the fluid being used in the IV therapy. Here, backflow program 112 may utilize the data stored in information repository 114 to determine what Red value, Green value, and Blue value to use as the standard values. In other words, standard values were previously input into for fluids and saved to information repository 114 either by a user via a user interface or imported as data from another device and stored in information repository 114. In this embodiment, fluids may have a standardized RGB color spectrum and therefore to have specific Red value, Green value, and Blue value that is considered a standard for the fluid. In a third embodiment, backflow program 112 may utilize the initial received RGB value, from step 202, as the standard value. In a simple example of the first embodiment, backflow program 112 may receive an input from a user of a standard value of Red value 225, Green value 217, and Blue value 223. In a simple example of the second embodiment, backflow program 112 may receive an indication that Fluid A is being used in IV therapy, backflow program 112 determines Fluid A has a standard value of Red value 225, Green value 217, and Blue value 223 from the information found in information repository 114. In a simple example of the third embodiment, backflow program 112 determined the received RGB values in step 202 to be Red value 225, Green value 217, and Blue value 223 and backflow program 112 sets these values as the standard values.

Once standard values are set, backflow program 112 sets a tolerance value. Here, a tolerance value is a deviation from the standard RGB values. In this embodiment, a tolerance value may be a numeric value or a percentage in either the negative or positive direction from the standard RGB values. In other words, backflow program 112 receives a manual input from a user that indicates a tolerance value. Alternatively, backflow program 112 may receive an indication to use tolerance values found in information repository 114, such as a specific tolerance value that a user has input previously and stored in information repository 114 to use for all fluids or a tolerance value that should be used for specific fluids. In a first example, using a numeric value, backflow program 112 sets a tolerance value of 10, therefore if the standard RGB values are Red value 225, Green value 217, and Blue value 223, then the tolerance value has a Red value of 215-235, Green value of 207-227, and Blue value of 213-233. In a second example, using a percentage, backflow program 112 sets a tolerance value of 10%, therefore if the standard RGB values are Red value 225, Green value 217, and Blue value 223, then the tolerance value has a Red value of 202.5-247.5, Green value of 195.3-238.7, and Blue value of 200.7-245.3.

Backflow program 112 receives updated RGB values (step 206). At step 206, backflow program 112 receives RGB values from sensor 120. Step 206 is substantially similar to Step 202. In an embodiment, backflow program 112 saves the received updated RGB values to information repository 114. In an embodiment, the updated RGB values are RGB values taken at a time period after the received RGB values in step 202.

Backflow program 112 determines whether the RGB value is within the tolerance values (decision step 208). At decision step 208, backflow program 112 determines whether the received updated RGB values at step 206 are within the tolerance values determined in step 204. In other words, are backflow program 112 determines whether each RGB value is within the tolerance values. In an embodiment, backflow program 112 determines whether any of the RGB values are within the tolerance values. In other words, is one of the three RGB values outside of the tolerance values. In an alternative embodiment, backflow program 112 determines whether all of the RGB values are within the tolerance values. In an embedment, if backflow program 112 determines the RGB values are within the tolerance values, processing proceeds to step 210. In an embodiment, if backflow program 112 determines the RGB values are outside the tolerance values, processing proceeds to step 212.

Backflow program 112 waits a time threshold (step 210). At step 210, backflow program 112 waits a time threshold before proceeding to step 206. In an embodiment, the time threshold may be in a range of 0.0001 seconds to 60 seconds. In an alternative embodiment, the time threshold may be any time able to be monitored by backflow program 112. In an embedment, the time threshold may be input by a user via the user interface of computing device 110. In an alternative embodiment, the time threshold may be input by a user via another device (not shown) and transmitted to backflow program 112 via computing device 110. In yet another embodiment, backflow program 112 may access information repository 114 to determine a time threshold to use, for example a standard time threshold always used by backflow program 112, a standard time threshold always used for a specific fluid, or a standard time threshold set by an organization (e.g., hospital, etc.)

Backflow program 112 provides an alarm (step 212). At step 212, backflow program 112 an indication to alarm 130. In an embodiment, alarm 130 as discussed above may provide an provide a haptic, audible, and/or visual indication. In a haptic example, alarm 130 may be a device that vibrates when an alarm in indicated and the vibration may be felt by the user. In an audible example, alarm 130 may be a speaker that makes a noise when an alarm is indicate and the noise may be heard by a user. In a visual example, alarm 130 may be a light that turns on or a specific color when an alarm is indicated, and the light may be seen by the user. In an alternative embodiment, alarm 130 may provide an indication to another computing device (not shown). For example, alarm 130 may indicate to a display in a nursing station that there is alarm and the nursing station may display the alarm. It should be noted, alarm 130 may be any combination of the above-referenced embodiments or may be only one of the above-referenced embodiments. Additionally, it should be noted that alarm 130 may be integrated into computing device 110.

Figure 3:
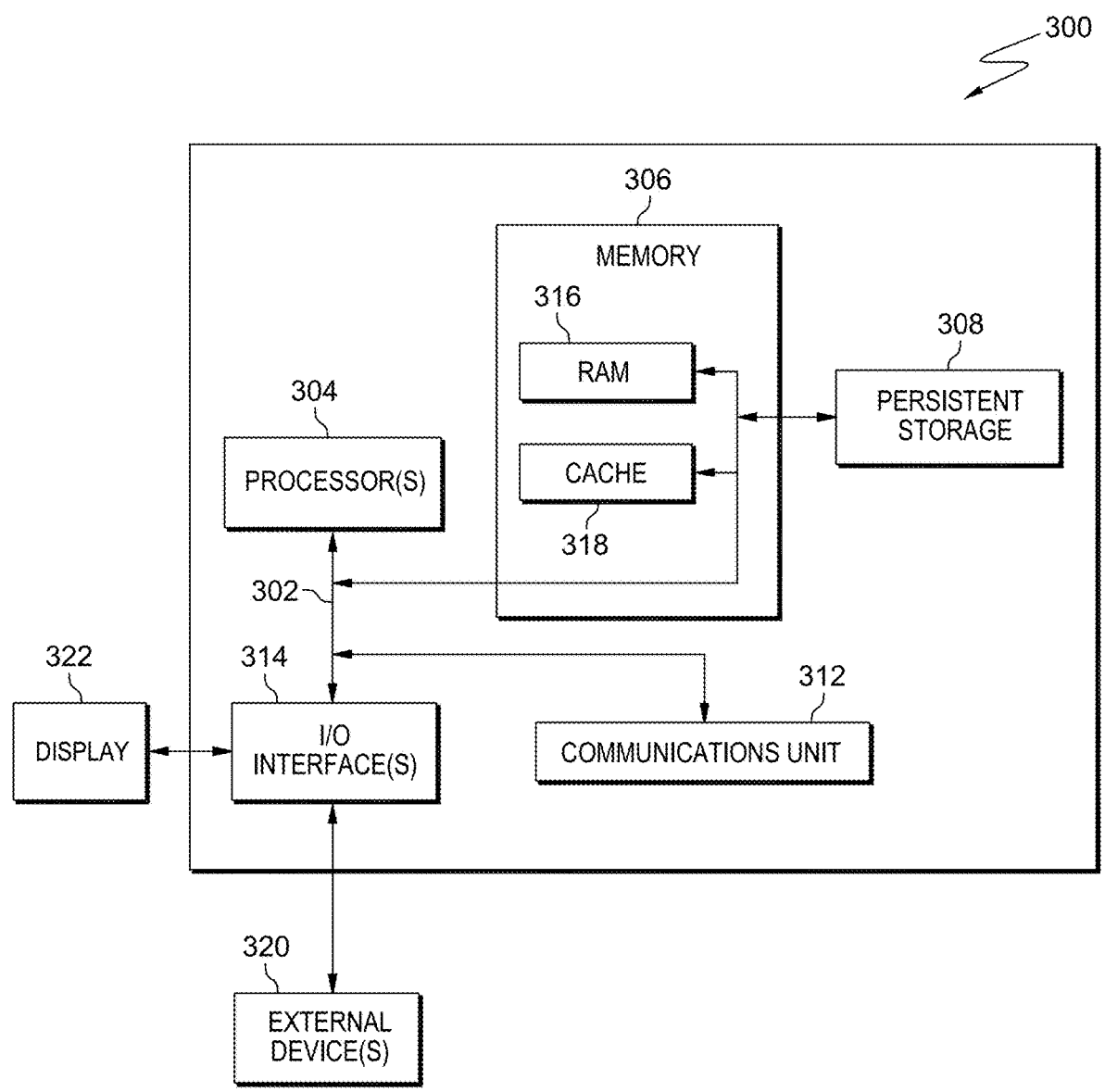
FIG. 3 is a block diagram depicting components of a computer, generally designated 300, suitable for executing backflow program 112, in accordance with at least one embodiment of the invention.

FIG. 3 is a block diagram depicting components of a computer 300 suitable for backflow program 112, in accordance with at least one embodiment of the invention. FIG. 3 displays the computer 300, one or more processor(s) 304 (including one or more computer processors), a communications fabric 302, a memory 406 including, a RAM 316, and a cache 318, a persistent storage 308, a communications unit 312, I/O interfaces 314, a display 322, and external devices 320. It should be appreciated that FIG. 3 provides only an illustration of one embodiment and does not imply any limitations with regard to the environments in which different embodiments may be implemented. Many modifications to the depicted environment may be made.

As depicted, the computer 300 operates over the communications fabric 302, which provides communications between the computer processor(s) 304, memory 306, persistent storage 308, communications unit 312, and input/output (I/O) interface(s) 314. The communications fabric 302 may be implemented with an architecture suitable for passing data or control information between the processors 304 (e.g., microprocessors, communications processors, and network processors), the memory 306, the external devices 320, and any other hardware components within a system. For example, the communications fabric 302 may be implemented with one or more buses.

The memory 306 and persistent storage 308 are computer readable storage media. In the depicted embodiment, the memory 306 comprises a random-access memory (RAM) 316 and a cache 318. In general, the memory 306 may comprise any suitable volatile or non-volatile one or more computer readable storage media.

Program instructions for backflow program 112 may be stored in the persistent storage 308, or more generally, any computer readable storage media, for execution by one or more of the respective computer processors 304 via one or more memories of the memory 306. The persistent storage 408 may be a magnetic hard disk drive, a solid-state disk drive, a semiconductor storage device, read only memory (ROM), electronically erasable programmable read-only memory (EEPROM), flash memory, or any other computer readable storage media that is capable of storing program instruction or digital information.

The media used by the persistent storage 308 may also be removable. For example, a removable hard drive may be used for persistent storage 308. Other examples include optical and magnetic disks, thumb drives, and smart cards that are inserted into a drive for transfer onto another computer readable storage medium that is also part of the persistent storage 308.

The communications unit 312, in these examples, provides for communications with other data processing systems or devices. In these examples, the communications unit 312 may comprise one or more network interface cards. The communications unit 312 may provide communications through the use of either or both physical and wireless communications links. In the context of some embodiments of the present invention, the source of the various input data may be physically remote to the computer 300 such that the input data may be received, and the output similarly transmitted via the communications unit 312.

The I/O interface(s) 314 allow for input and output of data with other devices that may operate in conjunction with the computer 300. For example, the I/O interface 314 may provide a connection to the external devices 320, which may be as a keyboard, keypad, a touch screen, or other suitable input devices. External devices 320 may also include portable computer readable storage media, for example thumb drives, portable optical or magnetic disks, and memory cards. Software and data used to practice embodiments of the present invention may be stored on such portable computer readable storage media and may be loaded onto the persistent storage 308 via the I/O interface(s) 314. The I/O interface(s) 314 may similarly connect to a display 322. The display 322 provides a mechanism to display data to a user and may be, for example, a computer monitor.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disk read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adaptor card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, though the Internet using an Internet Service Provider). In some embodiments, electronic circuitry including, for example programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram blocks or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of computer program instructions, which comprises one or more executable instructions for implementing the specified logical function(s). In some alternative implementations, the functions noted in the block may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing form the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A computer-implemented method for monitoring blood backflow in intravenous therapy, the computer-implemented method comprising:
   receiving, by one or more computer processors, a red, green, and blue values for a fluid, where the fluid is blood;
   determining, by one or more computer processors, a standard red, green, and blue values for the fluid,
   determining, by one or more computer processors, a tolerance red, green, and blue values for the fluid based on the standard red, green, and blue value for the fluid;
   determining, by a set of sensor device(s), updated red, green, and blue values for the fluid; and
   determining, by one or more computer processors, whether any of the updated red, green, and blue values for the fluid are outside of the associated tolerance red, green, and blue values for the fluid.

2. The computer-implemented method of claim 1, further comprising:
   responsive to determining that none of the updated red, green, and blue value for the fluid are outside of the associated tolerance red, green, and blue values for the fluid, indicating, by one or more computer processors, a time threshold; and
   responsive to meeting the time threshold, receiving, by one or more computer processors, a second updated red, green, and blue values for the fluid; and
   determining, by one or more computer processors, whether any of the second updated red, green, and blue values for the fluid are outside of the associated tolerance red, green, and blue values for the fluid.

3. The computer-implemented method of claim 1 wherein the determination of red, blue and green updated values includes using an infrared radiation blocking filter to reduce detection of infrared radiation spectral component by the set of sensor device(s).

4. The computer-implemented method of claim 3, wherein the alarm is selected from the group consisting of a haptic alarm, an audible alarm, and a visual alarm.

5. The computer-implemented method of claim 1, wherein the tolerance red, green, and blue values for the fluid based on the standard red, green, and blue value for the fluid are determined by a positive and negative percentage of the standard red, green, and blue value for the fluid.

6. The computer-implemented method of claim 1, wherein the standard red, green, and blue values for the fluid are the received red, green, and blue values for the fluid.

7. The computer-implemented method of claim 1, wherein the standard red, green, and blue values for the fluid are determined based on standardized red, green, blue color spectrum for the fluid.

8. A computer program product for monitoring blood backflow in intravenous therapy, the computer program product comprising:
  one or more computer readable storage media; and
  program instructions stored on the one or more computer readable storage media, the program instructions comprising:
    program instructions to receive a red, green, and blue values for a fluid, where the fluid is blood;
    program instructions to determine a standard red, green, and blue values for the fluid,
    program instructions to determine a tolerance red, green, and blue values for the fluid based on the standard red, green, and blue value for the fluid;
    program instructions to determine, by a set of sensor device(s), updated red, green, and blue values for the fluid; and
    program instructions to determine whether any of the updated red, green, and blue values for the fluid are outside of the associated tolerance red, green, and blue values for the fluid.

9. The computer program product of claim 8, further comprising program instructions stored on the one or more computer readable storage media, to:
  responsive to determining that none of the updated red, green, and blue value for the fluid are outside of the associated tolerance red, green, and blue values for the fluid, indicate a time threshold; and
  responsive to meeting the time threshold, receive a second updated red, green, and blue values for the fluid; and
  determine whether any of the second updated red, green, and blue values for the fluid are outside of the associated tolerance red, green, and blue values for the fluid.

10. The computer program product of claim 8 wherein the determination of red, blue and green updated values includes using an infrared radiation blocking filter to reduce detection of infrared radiation spectral component by the set of sensor device(s).

11. The computer program product of claim 10, wherein the alarm is selected from the group consisting of a haptic alarm, an audible alarm, and a visual alarm.

12. The computer program product of claim 8, wherein the tolerance red, green, and blue values for the fluid based on the standard red, green, and blue value for the fluid are determined by a positive and negative percentage of the standard red, green, and blue value for the fluid.

13. The computer program product of claim 8, wherein the standard red, green, and blue values for the fluid are the received red, green, and blue values for the fluid.

14. The computer program product of claim 8, wherein the standard red, green, and blue values for the fluid are determined based on standardized red, green, blue color spectrum for the fluid.

* * * * *